United States Patent [19]

Fischer

[11] Patent Number: Plant 5,536

[45] Date of Patent: Aug. 13, 1985

[54] AFRICAN VIOLET PLANT NAMED KATHRYN

[75] Inventor: Arnold Fischer, Hanover, Fed. Rep. of Germany

[73] Assignee: Pan American Plant Company, Parrish, Fla.

[21] Appl. No.: 539,805

[22] Filed: Oct. 7, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Kathryn, particularly characterized by its large dark blue single flowers having slightly ruffled petal margins; compact rosette habit, with the flowers being carried on erect peduncles; floriferous and intermittent year round flower habit, and by its medium green foliage.

1 Drawing Figure

1

The present invention comprises a new and distinct cultivar of African violet plant, botanically knows as *Saintpaulia ionantha,* and hereinafter referred to by the cultivar name Kathryn.

The new cultivar was referred to during the breeding and selection process by the designation V7-C56-B, and is a product of a planned breeding program. The basic objective of the breeding program was to create a new African violet cultivar having numerous large dark blue single flowers which stand erect above medium green foliage.

The new cultivar was originated from a cross made by applicant in a controlled breeding program in Hannover, Germany in 1976. The male and female parents are unknown at this time.

Kathryn was discovered and selected by applicant as a flowering plant within the progeny of the stated cross in a controlled environment in Fallbrook, Calif. in 1977. Asexual reproduction of the new cultivar by leaf cuttings, as performed by me at West Chicago, Ill., and Parrish, Fla., has demonstrated that the combination of characteristics as herein disclosed for the new cultivar are firmly fixed and retained through successive generations of asexual reproduction.

Kathryn has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Kathryn, which in combination distinguish this African violet as a new and distinct cultivar:

(1) Large dark blue single flowers.

(2) Slightly ruffled petal margins.

(3) Compact rosette habit, with flowers borne on upright peduncles.

(4) Suitable for production in 10 cm. pots, flowering in 10–12 weeks depending upon growing conditions.

(5) Very floriferous, with flowers continuing to develop for weeks after the onset of flowering.

(6) Medium green foliage, pubescent with crenate margin.

2

The new cultivar is most similar to Jackie, a cultivar of applicant disclosed in U.S. Plant Pat. No. 4,846. Kathryn is principally distinguished from Jackie by its darker green foilage, and its more consistantly floriferous habit.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 5000 foot candles of natural light at approximately 11:00 A.M. in Parrish, Fla.

Botanical classification: *Saintpaulia ionantha,* Ramat. cv. Kathryn.

Parentage:

*Male parent.*—Unknown.

*Female parent.*—Unknown.

Propagation: The new cultivar holds its distinguishing characteristics through successive propagations by leaf cuttings.

Plant: From 5 cm. to 9 cm. tall when grown in pots, and approximately 22 cm. in diameter when fully grown. The growth rate is normal, and the general shape of the fully grown plant is round.

*Leaves.*—Quantity: Abundant, Shape: Cordate with crenate margin. Diameter: 55–70 mm. Texture: Pubescent, glossy. Ribs and veins: Pinnate. Color (upperside): 147A. Color (underside): 147D between veins; veins 185B; there is a mixing of these colors in some interveinal areas. Petioles: 2–6 cm. long.

*Flowers.*—Buds: Size: Up to 1 cm.×1 cm. Shape: Round. Rate of opening: Normal. Color: Ranging from 87B to 87D to 84D. Sepals: Shape: Lanceolate. Color: 183D with show of 146D. Phyllaries: Two; lanceolate. Color: 146B Calyx: Shape: Funnel. Size: About 10–12 mm. in diameter. Aspect: Hairy. Peduncle: Length: 3–7 cm. Character: Erect and rigid. Color: 182A and 146D. Individual flowers: Number of petals: Five (5). Size: 30–35 mm. diameter and 7 mm. deep. Shape: Cup shaped when bloom first opens, becoming flat as flower matures. Color: Upperside: 86A. Underside: 87A. Flowers color will fade or darken depending upon light intensity, temperature and growth conditions. Borne: Cymose clusters formed on upright peduncles, 3–7 cm. long. Flowering habit: Flowers profusely and intermittently year round, with blooms lasting 2–3 weeks after which petals dry up but do not drop. Finishes in 10–12 weeks when a 2¼" plantlet is placed in a 10 cm. pot. Reproductive organs: Stamens: Borne singly on one side of the ovary; 2 anthers basifixed. Anthers: Two, basifixed; 2 mm.×2 mm., yellow. Filaments: 2–3 mm., purple-yellow. Pollen Color: Yellow. Pistels: Number: One. Style: 7–8 mm. long. Stigma: sticky, purple-white. Ovaries: Superior.

*Roots.*—Fine, fibrous.

*Disease resistance.*—No African violet diseases observed to date.

General observations: Kathryn has numerous dark blue flowers held on erect peduncles above medium green flat foliage with crenate leaf margins. The zygomorphic rotate flowers are single with five petals. Kathryn is finished in 10–12 weeks from a 2¼" plantlet in a controlled environment.

I claim:

1. A new and distinct cultivar of African violet plant named Kathryn, as described and illustrated, and particularly characterized by its large, dark blue single flowers having slightly ruffled petal margins; compact rosette habit, with the flowers being carried on erect peduncles; floriferous and intermittent year round flower habit, and by its medium green foliage.

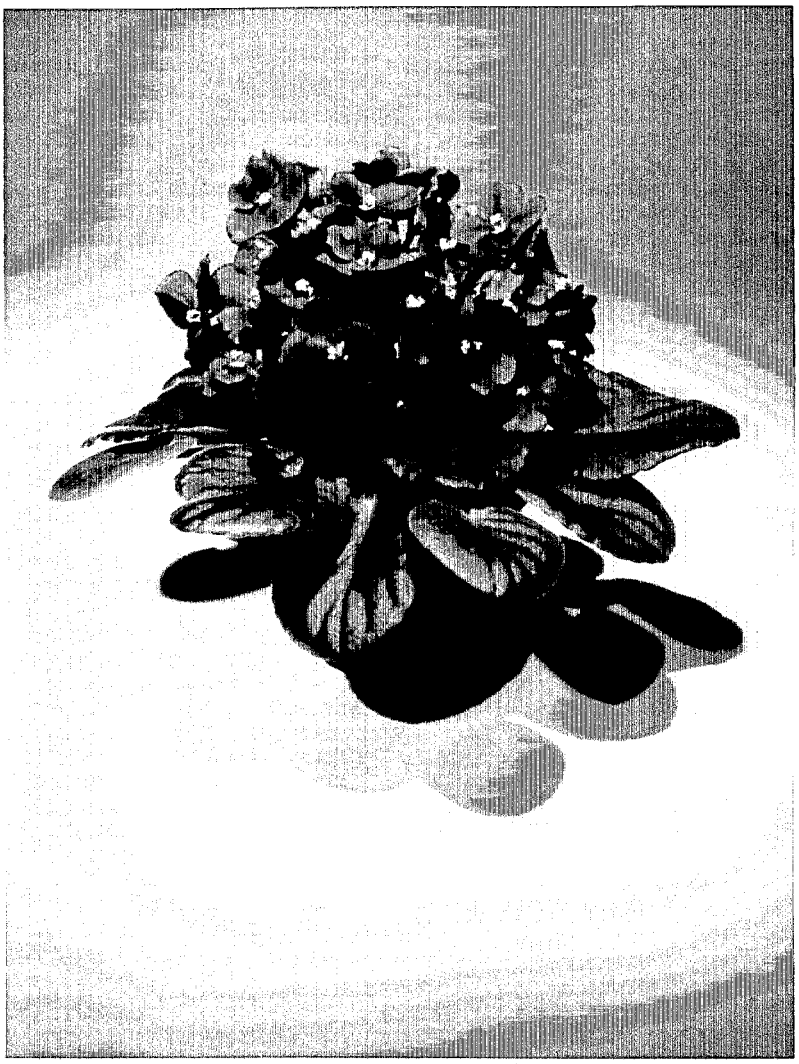

* * * * *